Figure 1:
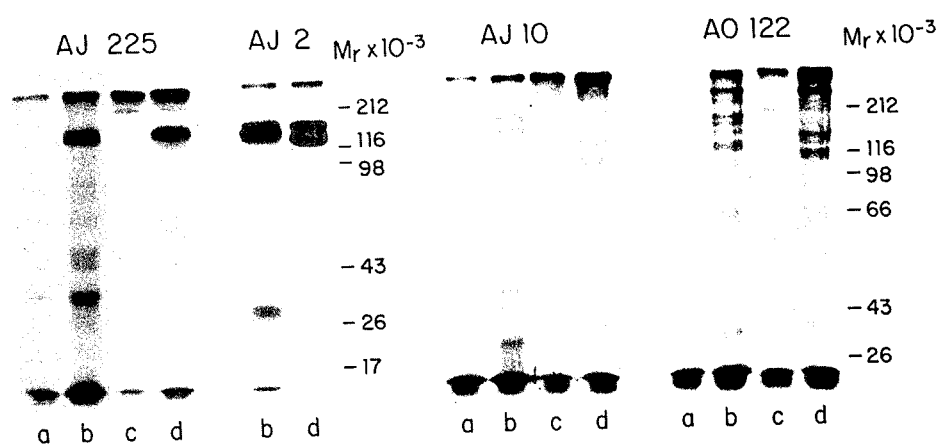

United States Patent [19]

Cairncross et al.

[11] Patent Number: 4,642,291

[45] Date of Patent: Feb. 10, 1987

[54] CELL SURFACE ANTIGENS OF HUMAN ASTROCYTOMA

[75] Inventors: J. Gregory Cairncross, London, Canada; M. Jules Mattes, Jamaica Estates, N.Y.; H. Richard Beresford, Centre Island, N.Y.; Anthony P. Albino; Alan N. Houghton, both of New York, N.Y.; Kenneth O. Lloyd, Bronx, N.Y.; Lloyd J. Old, New York, N.Y.

[73] Assignee: Sloan-Kettering Institute for Cancer Research, New York, N.Y.

[21] Appl. No.: 413,861

[22] Filed: Sep. 1, 1982

[51] Int. Cl.[4] .................... C12N 5/00; C12N 15/00; C12P 21/00; C12R 1/91
[52] U.S. Cl. .................................. 435/240; 436/548; 435/68; 435/172.2; 435/948; 935/104; 935/110
[58] Field of Search ............... 435/68, 172.2, 240, 435/241, 948; 436/548; 260/112 R

[56] References Cited

PUBLICATIONS

Schnegg et al, "Human Glioma-Associated Antigens Detected by Monoclonal Antibodies", Cancer Research, 41, pp. 1209–1213 (3–1981).
Herlyn et al, "Specific Immunoreactivity of Hybridoma-Secreted Monoclonal Anti-Melanoma Antibodies to Cultured Cells and Freshly . . . ", Cancer Research, 40, pp. 3602–3609 (1980).
Liao et al, "Common Neuroectodermal Antigens on Human Melanoma, Neuroblastoma, Retinoblastoma, Glioblastoma and Fetal Brain . . . ", European Journal of Immunology, 11, pp. 450–454 (6–1981).
Wikstrand et al, "Expression of Fetal Brain Antigens by Human Tumors of Neuroectodermal Origin as Defined by Monoclonal Antibody", Cancer Research, 42, pp. 267–275 (1–1982).
Carrel et al, "Expression of Neuroectodermal Antigens Common to Melanomas, Gliomas and Neuroblastomas", Acta Neuropathology, 57(2–3), pp. 158–164 (1982).
Wikstrand et al, "Human Fetal Brain Antigen Expression Common to Tumors of Neuroectodermal Tissue Origin", Journal of Neuroimmunology, 3(1), pp. 43–62 (8–1982).
Pfreundschuh et al, "Serological Analysis of Cell Surface Antigens of Malignant Human Brain Tumors", Proceedings of the National Academy of Sciences, 75(10), pp. 5122–5126, (1978).
Dippold et al, "Cell Surface Antigens of Human Malignant Melanoma: Definition of Six Antigenic Systems with Mouse Monoclonal Antibody", Proceedings of the National Academy of Sciences, 77(10), pp. 6114–6118 (1980).
Knowles et al, "Isolation and Characterization of Plasma Membranes from Transplantable Human Astrocytoma, Oat Cell Carcinoma . . . ", Cancer Research, 41, pp. 4131–4136 (1981).
Pukel et al, "GD3 A Prominent Ganglioside of Human Melanoma", Journal of Experimental Medicine, 155 (4), pp. 1133–1147 (4–1982).

Primary Examiner—Charles F. Warren
Assistant Examiner—John E. Tarcza
Attorney, Agent, or Firm—Felfe & Lynch

[57] ABSTRACT

Method of forming an antibody producing hybridoma cell line by fusing a myeloma cell line with splenocytes derived from BALB/c mice immunized with human astrocytoma tumor cells, the hybridoma cell line formed, and the monoclonal antibodies generated by said hybridoma cell line. A method of phenotyping astrocytoma tumor cells comprising determining the reaction of said cells to various monoclonal antibodies to astrocytoma tumor cells is also provided.

8 Claims, 4 Drawing Figures

CELL SURFACE ANTIGENS OF HUMAN ASTROCYTOMA

BACKGROUND

The present invention is concerned with various surface antigens of human cancer identified by mouse monoclonal antibodies and more particularly, with mouse monoclonal antibodies recognizing various antiogens expressed by human malignant astrocytoma.

Astrocytoma tumors are normally found only in the brain and are difficult to diagnose in a manner wherein a useful prognosis can be generated and the most effective treatment predicted. The present invention provides monoclonal antibodies which may be used in identifying or phenotying astrocytoma tumors whereby the course of the disease can be predicted and suitable therapy, e.g. chemotherapy versus radiotherapy—can be accomplished.

Furthermore, the present invention provides monoclonal antibodies which may be coupled with various side or toxic agents which then may be used for actual treatment or containment of astrocytoma tumors. Imaging of the tumor may also be possible using various radio labels; however, other means which are believed to be more practical, are available for this purpose.

The present invention also provides a process by which the inventive materials can be raised by sensitization of mice to raise the antibodies and the application of hybridoma fusion techniques to immortalize the cell line.

Work has been done in general with cell surface antigens of human cancers and cell surface antigens of human malignant melanoma and human renal cancer identified by mouse monoclonal antibodies have been described in the literature (1,2).

BRIEF DESCRIPTION

Abbreviations used in this disclosure: GFA, glial fibrillary acidic protein; AB, monoclonal antibody; EBV, Epstein-Barr virus; NP-40, Nonidet P40; conA, concanavalin A; PMSF, Phenylmethylsulfonylfluoride; PAGE, polyacrylamide gell electrophoresis; 2-D, two-dimensional electrophoresis; IEF, isoelectric focusing.

The surface antigens of cultured human malignant astrocytomas were analyzed using mouse monoclonal antibodies. BALB/c mice were immunized repeatedly with either SK-MG-1 [a glial fibrillary acidic protein (GFA)-negative astrocytoma line] or SK-A02 [a GFA-positive astrocytoma line]. Following fusion with NS/1 mouse myeloma cells, 12 antibody-producing clones were selected for detailed study. Serological analysis permitted the identification of 9 distinct antigen systems. Four antibodies (Ab AJ225, Ab A010, Ab AJ8, Ab A0122) identified cell surface antigens preferentially expressed on tumors of neuroectodermal origin, and these antibodies subdivided the astrocytoma panel into distinguishable subsets. The determinants detected by Ab A010 and Ab AJ8 showed mutually exclusive expression on the astrocytoma lines. The A010 and AJ8 phenotypes appeared to reflect the differentiation state of the cultured cells; 4/7 A010-positive astrocytomas expressed GFA, an intracellular astrocyte differentiation antigen, whereas all AJ8-positive astrocytomas (9/9) were GFA-negative. Five antibodies (Ab AJ10, Ab AJ9, Ab AJ17, Ab AJ425, Ab AJ2) recognized determinants widely distributed on normal and malignant cells. AJ2 was highly immunogenic in mice, and antibody to AJ2 was commonly found in the serum of mice immunized with human cells. Four antibodies defined in this study precipitated proteins from reduced preparations of radioisotope-labelled SK-MG-1 and SK-A02 cells: Ab AJ225 ($M_r$ 145,000), Ab A0122 ($M_r$ 265,000), Ab AJ10 ($M_r$s 195,000, 165,000) and Ab AJ2 ($M_r$s 170,000, 140,000, 140,000, 28,000).

IN THE DRAWINGS

FIG. 1 Autoradiograms of immunoprecipitates obtained with Ab AJ225, Ab AJ2, Ab AJ10 and Ab A0122 from $^{125}$I-labelled membrane extracts of SK-MG-1 and SK-A02 analyzed by NaDodSO$_4$/PAGE. Labelled SK-MG-1 cells were used for the analysis of Ab AJ225, Ab AJ2 and Ab AJ10 and labelled SK-A02 cells for the analysis of Ab A0122. Lanes (a) and (c) are control immunoprecipitates obtained with nu/nu mouse serum. (b) and (d) are immunoprecipitates obtained with the designated monoclonal antibody. Lanes (a) and (b) are reduced samples; (c) and (d) are non-reduced samples. Ab AJ225 and Ab AJ2 immunoprecipitates were analyzed with 9% acrylamide gels; Ab AJ10 and Ab A0122 immunoprecipitates with 7.5% acrylamide gels. Control immunoprecipitates for the analysis of Ab AJ2 were the same as those shown for Ab AJ225. Optimal immunoprecipitation was obtained with 1.0 μl Ab AJ225, 0.5 μl Ab A0122 and Ab AJ10, and 0.1 μl Ab AJ2. The molecular weight standards were myosin (212,000), β-galactosidase (116,000), phosphorylase (97,500), bovine albumin (66,000), ovalbumin (43,000), concanavalin A (26,000) and myoglobin (17,000).

Figure 2:
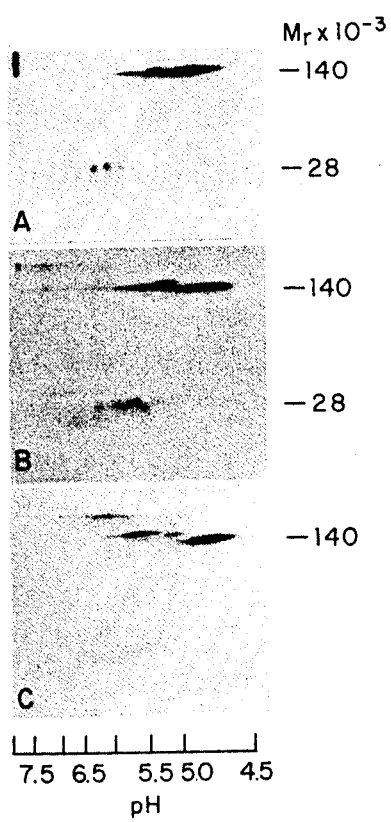

FIG. 2. Autoradiograms of immunoprecipitates obtained with Ab AJ2 from $^{125}$I-labelled SK-MG-1 membrane extracts analyzed by two-dimensional electrophoresis. Isoelectric focusing (IEF)(the first dimensional separation) was carried out in the horizontal direction, and NaDodSO$_4$/PAGE (the second dimensional separation) was carried out in the vertical direction on a 9% acrylamide gel. A: immunoprecipitates reduced before separation by IEF; B: immunoprecipitates reduced after separation by IEF; and C: unreduced immunoprecipitates. Control immunoprecipitates obtained with nu/nu mouse serum gave no significant spots.

Figure 3:
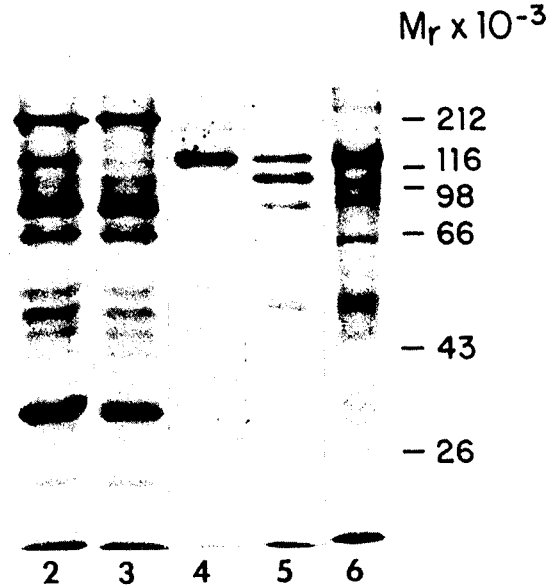

FIG. 3. Autoradiograms of immunoprecipitates obtained with (BALB/c×C57BL/6)F$_1$ mouse (CBF$_1$) antisera or Ab AJ2 from [$^{35}$S]methionine-labelled cultured human cell lines analyzed by NaDodSO$_4$/PAGE (9% gels). Lanes (a)–(e) are immunoprecipitates from labelled MeWo melanoma cell line; (f) is an immunoprecipitate from labelled 2774 ovarian cancer cell line. The precipitating antibodies were: (a) control: 3 μl normal CBF$_1$ mouse serum; (b) 3 μl CBF$_1$ anti-human ovarian cancer (2774) serum; (c) same as (b) but precleared with Ab AJ2; (d) 0.1 μl Ab AJ2; (e) 15 μl CBF$_1$ anti-human bladder cancer (RT-4) serum; (f) 3 μl CBF$_1$ anti-human ovarian cancer (SK-OV-3) serum.

Figure 4:
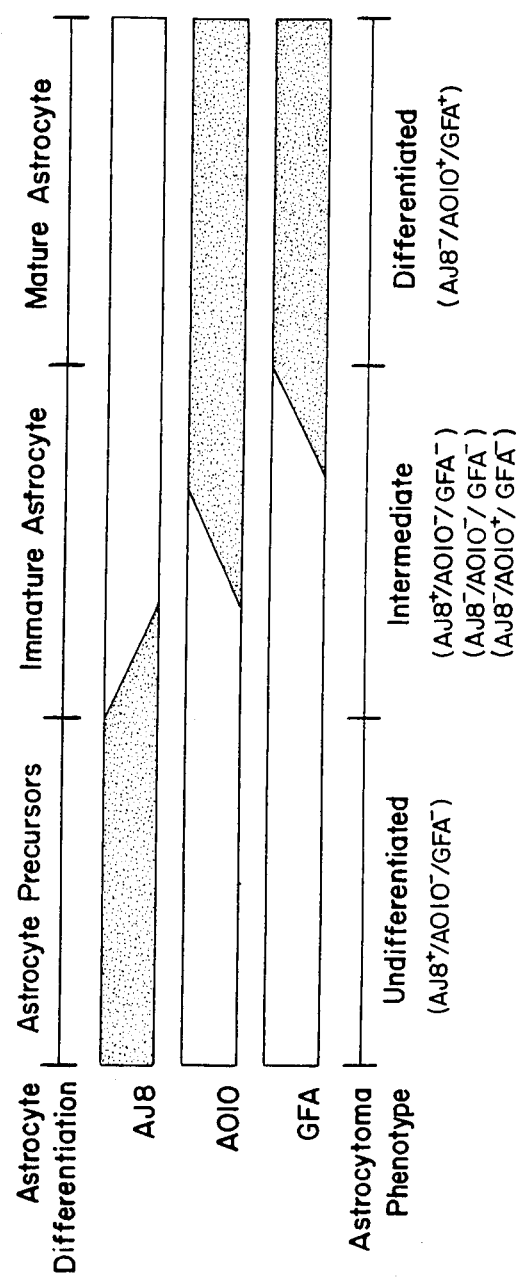

FIG. 4. Proposed relationship between astrocyte differentiation and phenotypic characteristics of cultured astrocytomas based on serological typing for AJ8, A010 and GFA.

DESCRIPTION

Tissue Culture

Astrocytoma and other human tumor cell lines and short-term cultures of normal human skin fibroblasts and kidney epithelial cells have been described (3,4,5).

Serological Procedures

Direct serological tests were performed using an anti-mouse Ig mixed hemadsorption assay (1). Direct test conditions and absorption procedures were identical to those previously described for the protein A-mixed hemadsorption assay (4). Heat stability of the antigenic determinants was assessed by heating the cell suspension to 100° C. for 5 minutes and then testing for residual antigenic activity in absorption tests. Glial fibrillary acidic protein (GFA) was demonstrated by indirect immunofluorescence using monospecific rabbit antiserum provided by Dr. L. F. Eng.

Immunizations

BALB/c mice were immunized with either the GFA-negative astrocytoma line SK-MG-1 [designated AJ in a previous publication (3)] or the GFA-positive astrocytoma line SK-A02 (established by J. R. Shapiro and W. R. Shapiro, Laboratory of Neuro-Oncology, Sloan-Kettering Institute). For the initial immunization, $1 \times 10^7$ astrocytoma cells were injected subcutaneously with Freund's complete adjuvant. Five to ten subsequent immunizations were carried out at 2-week intervals by intraperitoneal inoculation of $1 \times 10^7$ tumor cells in the absence of adjuvant. Immunized mice were sacrificed 3 days after the last injection.

Production of Mouse Monoclonal Antibodies

The fusion of immune spleen cells with mouse myeloma MOPC-21 NS/1 ATCC #T1B 18 cells (ratio 5:1) was performed as described (1,2). Fused cells were grown in selective medium and subcloned by limiting dilution as previously described (1,2). For initial screening, supernatants were tested for antibody activity on a panel of cultured cells consisting of 3 astrocytoma cell lines (including the immunizing line), 2 melanomas, 5 carcinomas and adult and fetal skin fibroblasts.

ATCC designations of screening cell lines are
HT-29 (HTB 38) (colon)
SK-MEL-28 (HTB 72) (melanoma)
SK-MEL-31 (HTB 73) (melanoma)
SK-ME-180 (HTB 33) (cervix)
T-24 (HTB 4) (bladder)
SK-N-SH (HTB 11) (neuroblastoma)
SK-N-MC (HTB 10) (neuroblastoma)
U-373 MG (HTB 17) (astrocytoma)
BT-20 (HTB 19) (breast)
MCF-7 (HTB 22) (breast)
SK-BR-3 (HTB 30) (breast).

Antibody subclass was determined by double diffusion in agar with anti-Ig heavy-chain-specific reagents (Bionetics, Kensington, MD). Cultures of cloned hybridomas were injected subcutaneously into nu/nu mice (NIH Swiss Background). Sera from mice with progressively growing tumors were used for serological and biochemical characterization.

Immunoprecipitation Procedures

Antibodies were tested for precipitating activity using radiolabelled antigen from detergent solubilized extracts of the immunizing cell line. Three different labelling procedures were used. Labelling with [$^3$H]glucosamine (New England Nuclear, 30-60 Ci/mmole) or with [$^{35}$S]methionine (New England Nuclear, 1000 Ci/mmole) and extraction with Nonidet P40 (NP-40) buffer were carried out as described previously (1,2). In some experiments the [$^{35}$S]methionine-labelled extract was fractionated on a 1 ml concanavalin A (conA)-Sepharose (Pharmacia, Piscattaway, NJ) column, using 0.15M NaCl, 0.01M Tris HCl pH 7.3, 0.1% NP-40 as column buffer, and eluting with 0.2M α-methyl D-mannoside. $^{125}$I-labelling of solubilized membrane preparations followed Brown et al (6), except that the gel filtration step before iodination was omitted. Membrane preparation was carried out according to Natori et al (7), except that the buffer during disruption was supplemented with 10 mM $MgCl_2$ and 2 mM phenylmethylsulfonylfluoride (PMSF). Protein-conjugated $^{125}$I was estimated by counting samples precipitated with cold 10% (w/v) trichloroacetic acid and then washed with ethanol and acetone.

Radioimmunoprecipitation procedures with [$^3$H]glucosamine- and [$^{35}$S]methionine-labelled samples were carried out as described (1,2). For $^{125}$I-labelled samples, aliquots (200 μl) were first precleared of non-specific binding material by treating with nu/nu mouse serum (1 μl), rabbit anti-mouse I gG (15 μl) (Cappel Laboratories, Cochranville, Pa) and *Staphylococcus aureus* (15 μl) (Bethesda Research Laboratories, Bethesda, Md). To aliquots (200 μl) of the precleared supernatant solution ($5 \times 10^5$ cpm $^{125}$I-protein), 0.1 or 1 μl antibody and 15 μl rabbit anti-mouse IgG were added. Immune complexes were isolated with *S. aureus* as described (6), except that 0.1 ml of normal rabbit serum was added to the second wash buffer to reduce background binding. Labelled antigen was eluted from the pellet and analyzed by $NaDodSO_4$/polyacrylamide gel electrophoresis (PAGE) and two-dimensional (2-D) electrophoresis as described previously (8,9), except that iodoacetamide (14 mg/ml) was added to the sample buffer when non-reduced samples were analyzed.

RESULTS

From 4 fusions of NS/1 myeloma with spleen cells from mice immunized with SK-MG-1 (3 fusions) or SK-A02 (1 fusion), 12 antibody-producing clones were selected for detailed analysis (Table 1). The serological specificity of these antibodies was tested on a panel of 49 established human cell lines (Table 2). The antibodies were also tested on short-term cultures of human adult and fetal skin fibroblasts, kidney epithelial cells and melanocytes. In most cases, serological analysis consisted of both direct and absorption tests. Melanocytes were studied only by direct test, and lymphoblastoid lines, erythrocytes, adult brain and fetal brain were analyzed only by absorption tests.

Monoclonal antibodies Ab AJ225, Ab A010, Ab AJ8, Ab A0122, Ab AJ10, Ab AJ9, Ab AJ17, Ab AJ425 and Ab AJ2 defined 9 distinct cell surface antigenic systems. They have been selected for detailed presentation (Table 2). [Of the remaining 3 monoclonal antibodies listed in Table 1, Ab A050 and Ab A092 were serologically related to Ab A0122, and Ab AJ60 was similar to Ab AJ10].

The above hybridoma cell lines are maintained and are available on deposit at Sloan-Kettering Institute for Cancer Research, 1275 York Avenue, New York, N.Y. 10022 under designations corresponding to the monoclonal antibodies produced by each hybridomas as follows:
AJ225
AJ8
A0122
AJ10
AJ9

AJ17
AJ425
AJ2
A010
A050
A092
AJ60

Upon granting of the patent, said hybridoma cell lines will be permanently available from the deposit with the American Type Culture Collection under ATCC designations corresponding to the above Sloan-Kettering designations as follows:

| SKI | ATCC |
|---|---|
| AJ225 | HB8344 |
| AJ8 | HB8339 |
| A0122 | HB8349 |
| AJ10 | HB8341 |
| AJ9 | HB8340 |
| AJ17 | HB8342 |
| AJ425 | HB8345 |
| AJ2 | HB8338 |
| A010 | HB8346 |
| AJ60 | HB8343 |
| A050 | HB8347 |
| A092 | HB8348 |

AJ225 Antigenic System

Direct tests and absorption analysis with Ab AJ225 indicated that the determinant detected by this antibody was largely restricted to astrocytoma cell lines (Table 2). Although all astrocytoma lines absorbed Ab AJ225 reactivity, the titers in direct serological tests permitted a division of cultured astrocytomas into two groups based upon quantitative differences in antigen expression; 12/16 tumors were high expressors and 4/16 low expressors. The only other tumor lines expressing high levels of AJ225 were 1/10 melanomas and 1/17 epithelial cancers; 2/4 renal carcinomas expressed low levels of the antigen demonstrable by absorption tests. In addition, a T-cell leukemia (MOLT-4) absorbed Ab AJ225 reactivity. EBV-transformed B-cells, adult and fetal skin fibroblasts, kidney epithelial cells, and homogenates of adult and fetal brain did not absorb. The results of direct serological tests on melanocytes suggest low levels of AJ225 expression on this normal cell type.

Ab AJ225 identified a heat-labile determinant and immunoprecipitated a protein with $M_r$ 145,000 from $^{125}$I-labelled SK-MG-1 (FIG. 1). This band was not detected in precipitates from cells labelled with [$^3$H]glucosamine or [$^{35}$S]methionine. In some experiments, this antigen appeared as a closely spaced doublet. The pI of the 145,000 $M_r$ component was 4.8. Without reduction a single band with $M_r$ 150,000 was identified relative to reduced standards. The inability to precipitate the AJ225 antigen after metabolic labeling raised the possibility that this determinant was a fetal calf serum component adsorbed to the cell surface. However, the highly restricted distribution of this antigen, the failure of fetal calf serum to inhibit Ab AJ225, and the ability of fresh astrocytoma tissue to absorb Ab AJ225 reactivity speak strongly against this possibility.

A010 and AJ8 Antigenic Systems

The A010 and AJ8 antigenic systems are described together because, with two exceptions, they subdivided 16 cultured astrocytomas into mutually exclusive A010-positive and AJ8-positive subsets. The exceptions were SK-MG-10 which expressed neither antigen and SK-MG-12 which expressed both.

The A010 antigen was identified on 7/16 astrocytoma lines. As shown in Table 2, 4/7 A010-positive astrocytomas were GFA-positive. The antigen was also demonstrated on 3/10 melanomas, 2/2 neuroblastomas, and a T-cell leukemia. Direct serological tests failed to demonstrate the A010 determinant on epithelial cancers; however, absorption of Ab A010 reactivity indicated low levels of antigen expression on 2/17 of these lines. EBV-transformed B-cells did not absorb Ab A010 reactivity. The A010 determinant was detected in adult and fetal brain but not identified on adult and fetal skin fibroblasts, kidney epithelial cells or melanocytes.

The AJ8 antigen was detected on 9/16 actrocytoma lines. All AJ8-positive astrocytomas were GFA-negative (Table 2). The AJ8 antigen was also demonstrated on 4/10 melanomas. Direct serological tests failed to demonstrate the AJ8 determinant on epithelial cancers; however, absorption analysis detected low levels of antigen expression on 4/17 cell lines. Neuroblastomas (0/2), EBV-transformed B-cells and a T-cell leukemia did not absorb Ab AJ8 reactivity. AJ8 was detected on adult and fetal skin fibroblasts and melanocytes, but not on cultured kidney epithelial cells or in adult or fetal brain.

The A010 determinant was heat-labile, suggesting that it resided on a protein, but Ab A010 did not precipitate a detectable component from [$^3$H]glucosamine-, [$^{35}$S]methionine-, or $^{125}$I-labelled SK-A02 cells. The AJ8 determinant was also heat-labile and could not be precipitated from [$^3$H]glucosamine-, [$^{35}$S]methionine-, or $^{125}$I-labelled SK-MG-1 cells.

A0122 Antigenic System

The A0122 antigen was found on 9/16 astrocytoma lines (Table 2). The pattern of expression on astrocytomas clearly distinguished the A0122 system from the AJ225, AJ8 or A010 systems. A0122 was strongly represented on 8/10 melanomas. Neuroblastomas (0/2), epithelial cancers (0/17), EBV-transformed B-cells, and a T-cell leukemia did not express A0122. Melanocytes and adult and fetal skin fibroblasts were highly reactive with Ab A0122, and homogenates of adult and fetal brain absorbed Ab A0122 reactivity. A0122 was not detected on kidney epithelial cells or erythrocytes.

Ab A0122 identified a heat-labile determinant and immunoprecipitated a protein complex from $^{125}$I-labelled SK-A02 cells. Four major proteins with $M_r$s 265,000, 195,000, 180,000 and 140,000 were identified in reduced preparations (FIG. 1). Without reduction, 4 components with $M_r$s 255,000, 150,000, 135,000 and 115,000 were seen. Only the 265,000 $M_r$ band was detected after labelling with [$^{35}$S]methionine. Ab A0122 did not precipitate a detectable component from [$^3$H]glucosamine labelled SK-A02 cells. Two other monoclonal antibodies, Ab A050 and Ab A092, appeared to recognize the A0122 determinant. The pattern of Ab A050 reactivity was identical to Ab A0122, but Ab A050 did not precipitate any components from $^{125}$I-labelled SK-A02 cells. Ab A092 precipitated the same protein complex as Ab A0122, although minor differences were found in the serological reactivity of the two antibodies.

AJ10 Antigenic System

The AJ10 determinant was found to be widely distributed on normal and malignant cells (Table 2). Despite this broad representation, the AJ10 antigen was not detected on any of the breat or colon cancer cell lines.

Ab AJ10 identified a heat-labile determinant and immunoprecipitated two clearly indentifiable proteins with $M_r$s 195,000 and 165,000 from reduced extracts of [$^{35}$S]methionine- or $^{125}$I-labelled SK-MG-1 cells (FIG. 1). Unreduced samples migrated as two bands corresponding to $M_r$S 135,000 and 110,000. Ab AJ10 did not precipitate a detectable component from [$^3$H]glucosamine-labelled cells. A second monoclonal antibody, Ab AJ60, demonstrated identical serological reactivity to Ab AJ10 but did not precipitate the 195,000/165,000 $M_r$ complex.

AJ2 Antigenic System

AJ2 was demonstrated on all nucleated human cells examined, both normal and malignant (Table 2). Ab AJ2 identified a heat-labile determinant and immunoprecipitated a glycoprotein complex from [$^3$H]glucosamine-, [$^{35}$S]methionine- and $^{125}$I-labelled SK-MG-1 cells. With $^{125}$I-labelling and under reduced conditions 3 components were identified by NaDodSO$_4$/PAGE: 2 heavy chains with $M_r$s 170,000 and 140,000 and one light chain with $M_r$ 28,000 (FIG. 1). Under non-reduced conditions, the 2 high molecular weight components migrated in a similar fashion, but the light chain was not identified (FIG. 1). 2-D electrophoresis resolved the 140,000 $M_r$ band into two distinct bands with slightly different molecular weights (FIG. 2). The 170,000 $M_r$ component had a pI of 5.2; the two 140,000 $M_r$ chains had isoelectric points of 5.5 and 4.7. The 28,000 $M_r$ light chain focused in 3 major spots at pH 6.2, 5.9 and 5.7 (FIG. 2A). The light chain was disulfide-linked to only one of the heavy chains. This was demonstrated in two ways. 2-D electrophoresis without reduction resulted in the disappearance of the light chain components and a shift upward of the 140,000 $M_r$ chain with pI 5.5 (FIG. 2C). Reduction after isoelectric focusing and before NaDodSO$_4$/PAGE demonstrated the light chain beneath the 140,000 $M_r$ chain with pI 5.5 (FIG. 2B). [$^{35}$S]methionine labelled the 4 submits, but the light chain very weakly. With [$^3$H]glucosamine-labelling, only the heavy chains were labelled. The [$^{35}$S]methionine-labelled SK-MG-1 membrane preparation was fractionated on a conA-Sepharose column; Ab AJ2 precipitated the 170,000/140,000/140,000/28,000 $M_r$s complex from the bound and eluted glycoprotein fraction.

Our experience suggests that AJ2 is highly immunogenic in mice. A range of antisera from mice hyperimmunized with different human cell lines immunoprecipitated a 140,000 $M_r$ component from [$^{35}$S]methionine-labelled cells (FIG. 3). Preclearing with Ab AJ2 removed this $M^r$140,000 component; preclearing with monoclonal antibodies of the same Ig subclass as Ab AJ2 but directed against other determinants did not remove the 140,000 $M_r$ band. In view of the strong immunogenicity of the AJ2 determinant, preclearing of AJ2 from cell extracts before immunizations may be advisable when antibodies to less immunogenic components are sought.

AJ9, AJ17 and AJ425 Antigenic Systems

Ab AJ9, Ab AJ17 and Ab AJ425 recognized heat-labile determinants on most normal and malignant cells. Differences in serological reactivity with specific cell lines suggest that they identify different antigenic systems. These antibodies have not precipitated detectable components from [$^3$H]glucosamine-, [$^{35}$S]methionine-, or $^{125}$I-labelled SK-MG-1 cells.

DISCUSSION

This study of human malignant astrocytoma has generated a series of mouse monoclonal antibodies that define nine distinct cell surface antigenic systems. These cell surface determinants have been characterized as restricted or widely distributed based on their distribution on a large panel of cultured tumor cell types. The restricted antigens (AJ225, A010, AJ8, A0122) are preferentially expressed on tumors of neuroectodermal origin. The non-restricted antigens (AJ10, AJ9, AJ17, AJ425, AJ2) are found on virtually all malignant cells. Cell surface determinants present only on tumor cells have not been detected in this analysis; the antigens described here have been identified as normal cell surface components by their expression on at least one normal cell type. The non-restricted antigenic systems are expressed on most normal cell types and are found in brain. The restricted systems, on the other hand, have a restricted distribution on normal cells as well. A010 and A0122 are detected in brain, AJ225 and AJ8 are not. The failure to identify the AJ225 and AJ8 determinants in brain suggests that within the context of normal neural cells AJ225 and AJ8 represent "tumor" antigens. However, end-point absorptions with homogenates of brain may not be sufficiently sensitive to detect antigens restricted to a small subpopulation of neural cells. Extending the serological analysis to sections of normal brain and astrocytomas will be important in assessing the significance of antigens detected on tumor cells in culture but not demonstrable in normal brain by absorption techniques or binding assays.

In this study, subsets of cultured astrocytomas have been identified. The biological significance of grouping astrocytomas on the basis of cell surface characteristics is unknown. Observations in other tumor systems suggest that the surface phenotype of transformed cells reflects both the cell of origin and the state of differentiation of the normal counterpart at the time of malignant change (10). Phenotypic differences among astrocytoma lines may be explained in one of three ways. Astrocytoma subsets may point to transformation in one of several developmentally and phenotypically distinct astrocyte lineages. Alternatively, tumor subsets may indicate that transformation has occurred at different points in a single lineage of astrocyte differentiation. Lastly, tumor subsets may reflect the random loss or random expression of astrocyte differentiation antigens.

The division of cultured astrocytomas into mutually exclusive A010-positive and AJ8-positive subsets and the relationship between the A010/AJ8 surface phenotype and GFA expression provide an opportunity to speculate on the biological significance of these cell surface markers and of the subsets they define. The intriguing feature of A010 and AJ8 expression is the essentially non-overlapping distribution on cultured astrocytomas. It is unlikely that subsetting of this kind is explained by a random expression or loss of the A010 and AJ8 determinants. However, this reciprocal relationship could be taken as evidence for the existence of two antigenically distinct astrocyte lineages or two antigenically distinct phases in a single lineage. Past studies of GFA have indicated that GFA is absent in pleuripotential neuroglial stem cells and immature astrocyte precursors but is detectable in all mature astrocytes (11). The observation that A010 is present on GFA-positive tumors and that AJ8-positive tumors are GFA-negative, suggests that these cell surface markers reflect the state of differentiation of astrocytomas in culture and lends support to the latter view that transformation has occurred in astrocytes at different points in a single developmental lineage.

Serological typing for AJ8, A010 and GFA suggests that cultured astrocytomas can be divided into three groups on the basis of differentiation-related phenotypic characteristics. Cultured astrocytomas which are AJ8-/A010+/GFA+ represent more differentiated cell lines; those which are AJ8+/A010-/GFA- represent less differentiated cell lines; and those which are AJ8-/A010+/GFA-, AJ8-/A010-/GFA- or AJ8+/A010+/GFA- represent groups at intermediate stages in differentiation. These relationships are illustrated in FIG. 4. It will now be important to determine whether this grouping of cultured astrocytomas on the basis of differentiation characteristics can be shown with tumors in vivo. Antigens AJ225 and A0122 also subset cultured astrocytomas, but the relationship between their expression and other biological properties of normal and malignant astrocytes is uncertain.

The reciprocal expression of A010 and AJ8 also extends to normal cells of neuroectodermal origin. Brain, for example, is A010+/AJ8−; melanocytes are A010−/AJ8+. Preliminary observations with other neuroectodermal tumors, including neuroblastoma and melanoma, indicate a similar pattern of reciprocal antigen expression. Also noteworthy is the detection of A010 on a T-cell leukemia (MOLT 4), a pattern reminiscent of that observed with other antigens, such as Thy-1, that are shared by T-cells and brain (12).

Because of differential serological methods, the use of different cell panels and the limited biochemical characterization of many determinants, especially those that do not precipitate, it is not possible to make direct comparisons between the antigens defined in this report and those described by other investigators in studies of malignant astrocytoma (13). Such comparisons await an exchange of reagents. However, serological differences on a uniform panel of cell lines together with immunochemical differences clearly distinguish the determinants described here from the 12 antigenic systems (gp 150, gp 95, $M_{19}$, $R_8$, $O_5$, $R_{24}$, gp160, $S_{25}$, gp120r, gp120nr, gp115, $V_1$) previously defined in our laboratory by mouse monoclonal antibodies to human malignant melanoma and human renal cancer (1,2,14).

It will be understood that the specification and examples are illustrative but not limitative of the present invention and that other embodiments and functional equivalents within the spirit and scope of the invention or by following the procedures outlined in the specification of this application will suggest themselves to, or be made by, those skilled in the art.

REFERENCES

1. Dippold, W. G., Lloyd, K. O., Li, L. T. C., Ikeda, H., Oettgen, H. F. and Old, L. J. (1980) Proc. Natl. Acad. Sci. USA 77, 6114–6118.
2. Ueda, R., Ogata, S-I., Morrissey, D. M., Finstad, C. L., Szkudlarek, J., Whitmore, W. F., Oettgen, H. F., Lloyd, K. O. and Old, L. J. (1981) Proc. Natl. Acad. Sci. USA 78, 5122–5126.
3. Pfreundschuh, M., Shiku, H., Takahashi, T., Ueda, R., Ransohoff, J., Oettgen, H. F. and Old, L. J. (1978) Proc. Natl. Acad. Sci. USA 75, 5122–5126.
4. Carey, T. E., Takahashi, T., Resnick, L. A., Oettgen, H. F. and Old, L. J. (1976) Proc. Natl. Acad. Sci. USA 73, 3278–3282.
5. Ueda, R., Shiku, H., Pfreundschuh, M., Takahashi, T., Li, L. T. C., Whitmore, W. F., Oettgen, H. F. and Old, L. J. (1979) J. Exp. Med. 150, 564–579.
6. Brown, J. P., Wright, P. W., Hart, C. E., Woodbury, R. G., Hellstrom, K. E. and Hellstrom, I. (1977) J. Biol. Chem. 255, 4980–4983.
7. Natori, T., Law, L. W. and Appella, E. (1977) Cancer Res. 37, 3406–3413.
8. O'Farrell, P. H. (1975) J. Biol. Chem. 250, 4007–4021.
9. Ogata S., Ueda, R. and Lloyd, K. O. (1981) Proc. Natl. Acad. Sci. USA 78, 770–774.
10. Magrath, I. T. (1981) J. Nat. Cancer Inst. 67, 501–514.
11. Juurlink, B. H. J., Fedoroff, S., Hall, C. and Nathaniel, E. J. H. (1981) J. Comp. Neurol. 200, 375–391.
12. Barclay, A. N., Letarte-Muirhead, M. and Williams, A. F. (1976) Nature 263, 563–567.
13. Schnegg, J. F., Diserens, A. C., Carrel, S., Accolla, R. S. and de Tribolet, N. (1981) Cancer Res. 41, 1209–1213.
14. Pukel, C. S., Lloyd, K. O., Travassos, L. R., Dippold, W. G., Oettgen, H. F. and Old, L. J. (1982) J. Exp. Med. 155, 1133–1147.

TABLE 1

DERIVATION OF MOUSE HYBRIDOMAS PRODUCING MONOCLONAL ANTIBODIES REACTING WITH SURFACE ANTIGENS OF HUMAN MALIGNANT ASTROCYTOMA CELLS

| Fusion No. | Astrocytoma cell line used for immunizations | No. of Immunizations | No. of positive wells/Total no. of wells | No. of clones isolated and analyzed | Antibodies Characterized |
|---|---|---|---|---|---|
| 1 | SK-MG-1 | 6 | 17/480 | 4 | AJ2 (1)*, AJ8 (1)*, AJ9 (1)*, AJ17 (1)* |
| 2 | SK-MG-1 | 6 | 10/480 | 3 | AJ60 (1), AJ225 (μ)* AJ425 (1)* |
| 3 | SK-MG-1 | 8 | 59/360 | 1 | AJ10 (1)* |
| 4 | SK-A02 | 10 | 20/360 | 4 | A010 (1)*, A050 (1), A092 (1), A0122 (1)* |

*Prototype antibodies (see Table 2)

TABLE 2

SEROLOGICAL CHARACTERIZATION OF NINE PROTOTYPE MOUSE MONOCLONAL ANTIBODIES DETECTING CELL SURFACE ANTIGENS ON HUMAN MALIGNANT ASTROCYTOMA CELLS

| Cells | Ab AJ225 Titer ×10⁻³ | Abs** | Ab AO10 Titer ×10⁻³ | Abs | Ab AJ8 Titer ×10⁻³ | Abs | Ab AO122 Titer ×10⁻³ | Abs | Ab AJ10 Titer ×10⁻³ | Abs | Ab AJ9 Titer ×10⁻³ | Abs | Ab AJ17 Titer ×10⁻³ | Abs | Ab AJ1425 Titer ×10⁻³ | Abs | Ab AJ2 Titer ×10⁻³ | Abs |
|---|---|---|---|---|---|---|---|---|---|---|---|---|---|---|---|---|---|---|
| Astrocytomas (GFA)* | | | | | | | | | | | | | | | | | | |
| SK-MG-1 (−) | 100 | + | — | — | 10 | + | — | — | 100 | + | 100 | + | 100 | + | 100 | + | 10000 | + |
| SK-MG-2 (+) | — | + | 10 | + | — | — | 100 | + | 100 | ++ | 1000 | ++ | 10 | ++ | — | ++ | 1000 | ++ |
| SK-MG-3 (−) | 10 | + | — | + | — | + | 1000 | ++ | 100 | ++ | 1000 | ++ | 10 | ++ | 100 | ++ | 10000 | ++ |
| SK-MG-4 (−) | 100 | + | 100 | + | — | — | 1000 | + | 10 | ++ | 1000 | ++ | 10 | ++ | 10 | + | 1000 | + |
| SK-MG-7 (−) | 100 | + | — | — | — | + | 100 | + | 10 | + | 1000 | ++ | 10 | ++ | — | + | 1000 | ++ |
| SK-MG-9 (−) | — | + | 100 | + | — | — | — | + | — | ++ | 100 | + | — | + | — | + | 1000 | + |
| SK-MG-10 (−) | 10 | + | — | — | 10 | ++ | 1000 | + | 100 | ++ | 100 | ++ | — | + | — | + | 1000 | + |
| SK-MG-11 (−) | 10 | + | 10 | + | 100 | ++ | — | — | — | ++ | 1000 | ++ | 100 | ++ | 100 | ++ | 10000 | ++ |
| SK-MG-12 (−) | 10 | + | — | — | 100 | + | 10 | + | 10 | ++ | 100 | ++ | — | ++ | 10 | ++ | 1000 | ++ |
| SK-MG-13 (−) | — | + | — | + | 100 | ++ | — | — | 100 | ++ | 100 | ++ | 10 | ++ | 100 | ++ | 1000 | ++ |
| SK-MS (−) | — | + | 1000 | + | — | + | 1000 | + | 10 | ++ | — | + | — | + | 10 | ++ | 1000 | + |
| SK-A02 (+) | 100 | + | — | — | 10 | + | — | — | 100 | ++ | 10 | + | 10 | ++ | 100 | ++ | 1000 | + |
| T98 (−) | — | + | — | — | — | — | — | — | — | — | — | — | — | — | — | — | — | — |
| U178MG (−) | 100 | ++ | — | ++ | 10 | — | — | — | 100 | ++ | 1000 | ++ | 10 | ++ | 100 | ++ | 1000 | ++ |
| U251MG (+) | — | ++ | 1000 | ++ | — | — | — | + | 100 | ++ | 1000 | ++ | 100 | ++ | 100 | ++ | 1000 | ++ |
| U373MG (+) | 100 | ++ | 1000 | ++ | — | — | — | ++ | 100 | ++ | 100 | ++ | 10 | ++ | 10 | ++ | 1000 | ++ |
| Neuroblastoma | | | | | | | | | | | | | | | | | | |
| SK NMC | — | + | 1000 | ++ | — | — | — | — | — | — | 1000 | + | 100 | + | 100 | ++ | 1000 | ++ |
| SK NSH | — | — | 100 | + | — | — | — | — | — | — | 1000 | ++ | — | — | — | — | 10000 | ++ |
| Melanoma | | | | | | | | | | | | | | | | | | |
| SK-MEL-13 | — | — | — | — | 1000 | ++ | 100 | ++ | 100 | ++ | 100 | ++ | — | ++ | 100 | ++ | 1000 | ++ |
| SK-MEL-28 | — | — | — | — | 1000 | ++ | 100 | + | 10 | + | 100 | ++ | 100 | ++ | 100 | ++ | 1000 | ++ |
| SK-MEL-29 | — | — | — | — | — | — | — | — | 1000 | ++ | 100 | ++ | 100 | ++ | 100 | ++ | 10000 | ++ |
| SK-MEL-31 | — | — | — | — | — | — | 1000 | ++ | 10 | ++ | 100 | ++ | 100 | ++ | 100 | ++ | 100 | ++ |
| SK-MEL-33 | — | — | — | — | — | — | — | — | 10 | ++ | 100 | ++ | 100 | ++ | 10 | ++ | 1000 | ++ |
| SK-MEL-37 | — | — | 10 | + | 1000 | + | 100 | ++ | 10 | ++ | 10 | ++ | 10 | ++ | — | ++ | 100 | ++ |
| SK-MEL-44 | 100 | + | — | — | — | — | 100 | + | 1000 | ++ | 100 | ++ | 100 | ++ | 1000 | ++ | 1000 | ++ |
| SK-MEL-93 | — | — | — | — | 1000 | + | 100 | + | 1000 | ++ | 100 | ++ | 100 | ++ | 10 | ++ | 100 | ++ |
| SK-MEL-124 | — | — | — | — | — | — | 100 | ++ | — | — | 100 | + | 100 | ++ | 10 | ++ | 1000 | ++ |
| MeWo | — | — | — | — | 10000 | + | 1000 | ++ | — | — | 1000 | + | 100 | ++ | 10 | ++ | 1000 | ++ |
| EPITHELIAL CANCERS | | | | | | | | | | | | | | | | | | |
| Lung | | | | | | | | | | | | | | | | | | |
| SK-LL-LC | 10 | + | — | — | — | — | — | — | — | — | — | + | 1 | ++ | — | ++ | 100 | ++ |
| SK-LC-6 | — | + | — | — | — | — | — | — | 100 | + | 10 | + | 10 | ++ | 100 | ++ | 10000 | ++ |
| Breast | | | | | | | | | | | | | | | | | | |
| A1Ab | — | — | — | — | — | — | — | — | — | — | 1000 | ++ | 10 | ++ | 100 | ++ | 1000 | ++ |
| BT-20 | — | — | — | — | — | — | — | — | — | — | 1000 | — | 10 | ++ | — | ++ | 1000 | ++ |
| CAMA | — | — | — | — | — | — | — | — | — | — | — | — | 10 | ++ | 100 | ++ | 1000 | +++ |
| MCF-7 | — | — | — | — | — | — | — | — | — | — | 100 | + | 100 | ++ | — | ++ | 1000 | ++ |
| SK-BR-3 | — | — | — | — | — | — | — | — | — | — | 100 | ++ | 10 | ++ | — | ++ | 1000 | ++ |
| Colon | | | | | | | | | | | | | | | | | | |
| HT-29 | — | — | — | — | — | — | — | — | — | — | 100 | ++ | — | +++ | — | +++ | 1000 | +++ |
| SW-1116 | — | — | — | — | — | — | — | — | — | — | 100 | ++ | — | — | — | — | 1000 | ++ |
| SW-1222 | — | — | — | — | — | — | — | — | — | — | 100 | + | — | — | — | — | 1000 | ++ |

TABLE 2-continued

SEROLOGICAL CHARACTERIZATION OF NINE PROTOTYPE MOUSE MONOCLONAL ANTIBODIES DETECTING CELL SURFACE ANTIGENS ON HUMAN MALIGNANT ASTROCYTOMA CELLS

| Cells | Ab AJ225 Titer* $\times 10^{-3}$ | Abs** | Ab A010 Titer $\times 10^{-3}$ | Abs | Ab AJ8 Titer $\times 10^{-3}$ | Abs | Ab A0122 Titer $\times 10^{-3}$ | Abs | Ab AJ10 Titer $\times 10^{-3}$ | Abs | Ab AJ9 Titer $\times 10^{-3}$ | Abs | Ab AJ17 Titer $\times 10^{-3}$ | Abs | Ab AJ425 Titer $\times 10^{-3}$ | Abs | Ab AJ2 Titer $\times 10^{-3}$ | Abs |
|---|---|---|---|---|---|---|---|---|---|---|---|---|---|---|---|---|---|---|
| Renal | | | | | | | | | | | | | | | | | | |
| SK-RC-1 | — | + | — | — | — | + | — | — | 100 | + | 100 | + | 10 | + | 100 | + | 1000 | + |
| SK-RC-6 | — | — | — | + | — | — | — | — | 100 | + | 100 | + | 10 | + | 100 | + | 10000 | + |
| SK-RC-7 | — | — | — | — | — | — | — | — | 100 | + | 100 | + | 10 | + | 100 | + | 1000 | + |
| SK-RC-9 | — | + | — | — | — | + | — | — | 1000 | + | 100 | + | 10 | + | 100 | + | 1000 | + |
| Bladder | | | | | | | | | | | | | | | | | | |
| RT-4 | — | — | — | + | — | — | — | — | — | — | — | + | — | — | — | — | 10 | + |
| T-24 | — | — | — | — | — | — | — | — | 100 | + | 1000 | + | 1000 | + | 1000 | + | 10000 | + |
| Cervix | | | | | | | | | | | | | | | | | | |
| ME-180 | — | — | — | — | — | — | — | — | — | — | 100 | + | — | — | — | + | 100 | + |
| LYMPHOBLASTOID CELLS | | | | | | | | | | | | | | | | | | |
| EBV B-cells | | | | | | | | | | | | | | | | | | |
| AH | — | — | — | — | — | — | — | — | — | — | — | — | — | — | — | — | — | + |
| BT | — | — | — | + | — | — | — | — | — | + | — | + | — | + | — | + | — | + |
| BD | — | — | — | — | — | — | — | + | — | — | — | — | — | — | — | — | — | — |
| T-cells | | | | | | | | | | | | | | | | | | |
| MOLT-4 | — | + | — | + | — | + | 100 | — | — | — | — | — | — | — | — | + | — | + |
| NORMAL HUMAN CELLS | | | | | | | | | | | | | | | | | | |
| Main | | | | | | | | | | | | | | | | | | |
| Adult | — | — | — | — | — | — | 10 | — | — | + | — | + | 100 | + | 1 | — | 1000 | + |
| Fetal | | | | | | | | | | | | | | | | | | |
| Adult skin fibroblasts | — | — | — | — | — | — | — | — | — | — | — | — | — | — | — | — | — | — |
| Fetal skin fibroblasts | — | — | — | — | — | — | — | — | 100 | + | 100 | + | 10 | + | 100 | + | 1000 | + |
| Adult kidney epithelium | — | — | — | — | — | — | 100 | — | 1000 | + | 100 | + | 10 | + | 100 | + | 1000 | + |
| lanocytes | 1 | — | — | — | 10 | — | 100 | — | — | — | — | — | — | — | — | — | — | — |
| erythrocytes | — | — | — | — | — | — | — | — | — | — | — | — | — | — | — | — | — | — |

*Titer: — indicates no reaction in direct tests at a dilution of 1:100.
**Abs: absorption tests. Sera (diluted to end point) were absorbed with the indicated cell type and tested for residual activity for SK-MG-1 (Ab AJ225, Ab AJ10, Ab AJ9, Ab AJ17, Ab AJ425, Ab AJ2), U251MG (Ab A010), or SK-MEL-28 (Ab AJ8, Ab A0122); +, complete absorption; —, no absorption.
***GFA: Glial fibrillary acidic protein expression was determined by reactivity of cultured astrocytoma cells (formaldehyde/acetone fixed) with rabbit anti-GFA antiserum (Dilution: 1/500) in indirect immunofluorescence tests.

What is claimed is:

1. Two or more monoclonal anbibodies capable of restricted and non-restricted binding to two or more human astrocytoma cell antigens and capable of subsetting malignant human astrocytoma cells into successive differentiation states wherein said restricted monoclonal antibody is selected from the group consisting of AJ8, AJ225, A010, A050, A092 and A0122 and said non-restricted monoclonal antibody is selected from the group consisting of AJ2, AJ9, AJ10, AJ17, AJ60 and AJ425, and wherein said monoclonal antibody is capable of subsetting human astrocytomas into antibody binding classes selected from the group consisting of: AJ8 positive/A010 negative/GFA negative, AJ8 negative/A010 positive/GFA positive and AJ8 negative/A010 positive/GFA negative.

2. Monoclonal antibody producing hybridoma cell lines characterized by the production of the monoclonal antibodies of claim 1.

3. Monoclonal antibodies of claim 1 comprising a panel for the diagnosis of human astrocytoma.

4. Method for differentiating between normal human astrocyte cells and abnormal human astrocytoma cells or differentiating between astrocytoma cells which comprises contacting a human astrocyte or astrocytoma cell specimen with at least two of the monoclonal antibodies of claim 1 and detecting one or more malignant astrocytoma cell antigens reacting with said antibody.

5. Method of phenotyping human astrocytoma cells which comprises contacting a human astrocytoma cell or tissue specimen with each of the monoclonal antibodies of claim 1, observing the antigen-antibody response, and determining the presence or absence of GFA.

6. Monoclonal antibody panel of claim 1 consisting of two or more of the monoclonal antibodies selected from the group consisting of AJ8, AJ225, A010, A050, A092 and A0122.

7. A test kit for differentiating human astrocytomas comprising monoclonal antibodies AJ8 and A010 in amounts sufficient to be capable of subsetting human astrocytomas into antibody binding classes, when used together with GFA testing reagents, wherein the astrocytoma classes are selected from the group consisting of AJ8 positive/A010 negative/GFA negative, AJ8 negative/A010 positive/GFA positive and AJ8 negative/A010 positive/GFA negative.

8. Method of subsetting human astrocytomas which comprises contacting a human astrocytoma specimen with monoclonal antibody AJ8 and A010 separately, observing an antigen-antibody reaction or lack thereof and determining the presence or absence of GFA.

* * * * *